US010945796B2

(12) United States Patent
Popovic et al.

(10) Patent No.: US 10,945,796 B2
(45) Date of Patent: Mar. 16, 2021

(54) ROBOTIC CONTROL OF SURGICAL INSTRUMENT VISIBILITY

(71) Applicant: KONINKLIJKE PHILIPS N.V., Eindhoven (NL)

(72) Inventors: Aleksandra Popovic, Boston, MA (US); David Paul Noonan, New York, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 394 days.

(21) Appl. No.: 15/117,001

(22) PCT Filed: Jan. 29, 2015

(86) PCT No.: PCT/IB2015/050665
§ 371 (c)(1),
(2) Date: Aug. 5, 2016

(87) PCT Pub. No.: WO2015/121765
PCT Pub. Date: Aug. 20, 2015

(65) Prior Publication Data
US 2016/0354166 A1  Dec. 8, 2016

Related U.S. Application Data

(60) Provisional application No. 61/938,721, filed on Feb. 12, 2014.

(51) Int. Cl.
*A61B 34/30* (2016.01)
*A61B 1/00* (2006.01)
(Continued)

(52) U.S. Cl.
CPC .......... *A61B 34/30* (2016.02); *A61B 1/00006* (2013.01); *A61B 1/00009* (2013.01);
(Continued)

(58) Field of Classification Search
CPC . A61B 34/30; A61B 1/00006; A61B 1/00009; A61B 1/00011; A61B 1/00045;
(Continued)

(56) References Cited

U.S. PATENT DOCUMENTS 5,417,210 A  5/1995 Funda
5,911,036 A  6/1999 Wright
(Continued)

FOREIGN PATENT DOCUMENTS

WO  2013027200 A2  2/2013
WO  2013093761 A2  6/2013

OTHER PUBLICATIONS

Voros, Sandrine et al "Automatic Detection of Instruments in Laparoscopic Images: A First Step Towards High-Level Command of Robotic Endoscopic Holders", The International Journal of Robotics Research, vol. 26, 2007.

*Primary Examiner* — Timothy J Neal
*Assistant Examiner* — William B Chou

(57) ABSTRACT

A robot guiding system employing a robot unit (10) including an endoscope (12) and a robot (11), and a control unit (20) including an endoscopic image controller (22) and a robot controller (21). In operation, the endoscope (12) generate an endoscopic image of an anatomical region as the robot (11) move the endoscope (12) within the anatomical region in response to robot actuator commands. The endoscopic image controller (22) controls a display of the endoscopic image (14) of the anatomical region and generates endoscope pose commands to maintain a visibility of two or more interventional instruments within the display of the endoscopic image (14) relative to a center of the endoscopic image (14). The robot controller (21) generates the robotic actuator commands responsive to the endoscope pose commands.

16 Claims, 6 Drawing Sheets

(51) Int. Cl.
  *A61B 1/045* (2006.01)
  *A61B 1/313* (2006.01)
  *A61B 17/00* (2006.01)
  *A61B 34/20* (2016.01)

(52) U.S. Cl.
  CPC ...... *A61B 1/00045* (2013.01); *A61B 1/00133* (2013.01); *A61B 1/00149* (2013.01); *A61B 1/045* (2013.01); *A61B 1/3132* (2013.01); *A61B 17/00234* (2013.01); *A61B 2034/2057* (2016.02); *A61B 2034/2065* (2016.02); *A61B 2034/301* (2016.02)

(58) Field of Classification Search
  CPC .............. A61B 1/0005; A61B 1/00133; A61B 1/00149; A61B 1/00188; A61B 1/045; A61B 1/3132; A61B 17/00234
  USPC ....... 600/102, 103, 104, 106, 108, 109, 113, 600/114, 117, 118, 126, 145, 146, 153, 600/160
  See application file for complete search history.

(56) References Cited

U.S. PATENT DOCUMENTS

| | | |
|---|---|---|
| 7,447,537 B1 | 11/2008 | Funda |
| 2005/0033580 A1 | 2/2005 | Wang |
| 2008/0234866 A1 | 9/2008 | Kishi |
| 2008/0262297 A1* | 10/2008 | Gilboa ............... A61B 1/00128 600/109 |
| 2009/0074265 A1* | 3/2009 | Huang ................... A61B 1/041 382/128 |
| 2009/0088773 A1 | 4/2009 | Zhao |
| 2009/0245600 A1 | 10/2009 | Hoffman |
| 2009/0326553 A1* | 12/2009 | Mustufa ................ A61B 90/36 606/130 |
| 2010/0111389 A1* | 5/2010 | Strobel .................... A61B 6/12 382/131 |
| 2010/0217075 A1* | 8/2010 | Shigeta ............. A61B 1/00009 600/104 |
| 2010/0274087 A1* | 10/2010 | Diolaiti ................. A61B 34/37 600/118 |
| 2010/0331856 A1 | 12/2010 | Carlson |
| 2012/0154564 A1 | 6/2012 | Hoffman |
| 2012/0307027 A1 | 12/2012 | Popovic |
| 2013/0211588 A1 | 8/2013 | Diolaiti |
| 2014/0049626 A1* | 2/2014 | Ishihara ............. A61B 1/00009 348/68 |
| 2015/0138329 A1* | 5/2015 | Braun .................. A61B 5/6861 348/71 |
| 2016/0314710 A1* | 10/2016 | Jarc ....................... G09B 23/285 |
| 2018/0324414 A1* | 11/2018 | Hoffman .............. H04N 13/156 |

* cited by examiner

ROBOTIC CONTROL OF SURGICAL INSTRUMENT VISIBILITY

CROSS-REFERENCE TO PRIOR APPLICATIONS

This application is the U.S. National Phase application under 35 U.S.C. § 371 of International Application No. PCT/IB2015/050665, filed on Jan. 29, 2015, which claims the benefit of U.S. Provisional Patent Application No. 61/938,721, filed on Feb. 12, 2014. These applications are hereby incorporated by reference herein.

The present invention generally relates to robotic control of an endoscope during a minimally invasive surgical procedure (e.g., a minimally invasive coronary bypass grafting surgery). The present invention specifically relates to maintaining a visibility of surgical instruments within an endoscopic image.

Minimally invasive surgery is performed using elongated instruments inserted into a patient's body through small ports. An endoscopic camera is also inserted into the patient via a small port to provide visualization of the instruments relative to the surgical site. For example, FIG. 1 shows elongated instruments 30 inserted into a patient's body through small ports and endoscopic camera 12 also inserted into a patient's body through small ports to provide visualization of instruments 30 relative to the surgical site.

Currently, a surgeon holds and manually controls the two (2) surgical instruments during surgery, and a physician assistant controls the endoscope and receives instructions from the surgeon to move the endoscope to specific locations during surgery. Communicating the exact desired location of the endoscope to the physician assistant is difficult, especially given the challenging hand-eye coordination required to move the endoscope and instruments around the pivot points at the entrance to the body, and given the different positions and frames of reference of the surgeon, physician assistant and video image. For example, "Left" on the video image, may mean "right and down" at the physician assistant's hands.

To overcome these difficulties, controlling the endoscope using an automated device or robot (e.g., robot 11 shown in FIG. 1) has been proposed in prior art, essentially removing the physician assistant from this task during surgery. However, given that the surgeon is controlling two (2) instruments with both hands, the method with which the physician may control the robotic endoscope is important and a number of propositions have been addressed in prior art.

For example, one proposition proposes optical targets being placed on a surgical instrument to allow the robotic endoscope to be positioned so that the markers are in the center of the image. Known input devices for guidance of the robotic endoscope to position the markers in the center of the image include, but are not limited to, head motion sensors, joysticks and voice control. Alternatively, the robotic endoscope may be guided from live endoscope images by determining a three-dimensional ("3D") position of an anatomical feature with respect to the endoscope and moving the endoscope or a surgical instrument toward the anatomical feature.

The abovementioned proposition assumes that an operating surgeon is responsible to keep the instruments in the field-of-view of the endoscope. In practice, two problems commonly arise: First, the surgeon typically moves one or both instruments outside of the endoscope view. Second, the robotic system may rotate around its own axis changing the spatial arrangement of instruments on the screen. Both of these situations are highly challenging and risky. Additionally, the aforementioned proposition involves a calibrated endoscope to perform the motion. However, calibration of an endoscope is technically challenging for medical staff and preferably should be avoided.

To address these drawbacks the present invention provides guidance of the robotic endoscope whereby all relevant instruments are always visible in an endoscopic field. The present invention further provided guidance of the robotic endoscope whereby an appropriate rotation and zooming of the endoscope is achieved.

One form of the present invention a robot guiding system employing a robot unit including an endoscope and a robot, and a control unit including an endoscopic image controller and a robot controller. In operation, the endoscope generate an endoscopic image of an anatomical region as the robot moves the endoscope within the anatomical region in response to robot actuator commands. The endoscopic image controller controls a display of the endoscopic image of the anatomical region and generates endoscope pose commands to maintain a visibility of two or more interventional instruments within the display of the endoscopic image relative to a center of the endoscopic image. The robot controller generates the robotic actuator commands responsive to the endoscope pose commands.

A second form of the present invention is a robot guiding method involving an operation of an endoscope to generate and display an endoscopic image of an anatomical region, and a commanding a robot to move the endoscope within the anatomical region as the endoscope is generating the endoscopic image of the anatomical region. The commanding of the robot maintains a visibility of two or more interventional instruments within the display of the endoscopic image relative to a center of the endoscopic image.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

Figure 2:
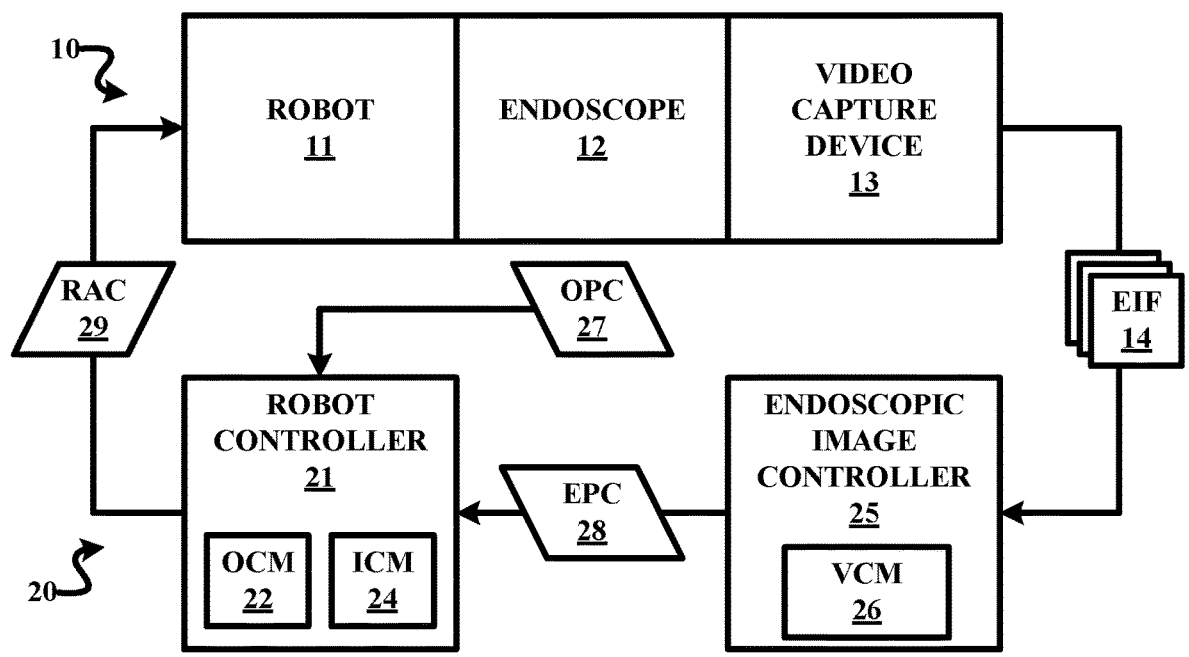
FIG. 2 illustrates an exemplary embodiment of a robotic guiding system in accordance with the present invention.

As shown in FIG. 2, a robotic guiding system employs a robot unit 10 and a control unit 20 for any endoscopic procedure involving an endoscopic imaging of an anatomical region (e.g., cranial region, thoracic region, abdominal region, patellar region, etc.). Examples of such endoscopic procedures include, but are not limited to, minimally invasive cardiac surgery (e.g., coronary artery bypass grafting or mitral valve replacement), laparoscopic surgery (e.g., hysterectomy, prostatectomy and gall bladder surgery), natural orifice transluminal surgery (NOTES), single incision laparoscopic surgery (SILS), pulmonary/bronchoscopic surgery and minimally invasive diagnostic interventions (e.g., arthroscopy).

Robot unit 10 includes a robot 11, an endoscope 12 rigidly attached to robot 11 and a video capture device 13 attached to endoscope 12.

Robot 11 is broadly defined herein as any robotic device structurally configured with motorized control of one or more joints for maneuvering an end-effector as desired for the particular robotic procedure. In practice, robot 11 has a minimum of two (2) degrees-of-freedom to ensure all instruments are always visible in an endoscopic field, robot 11 has a minimum of three (3) degrees-of-freedom for zooming the visible instruments in and out of the endoscopic field, and robot has a minimum of four (4) degrees-of-freedom for a rotation of the visible instruments within the endoscopic field.

Endoscope 12 is broadly defined herein as any device structurally configured with ability to image from inside a body. Examples of endoscope 12 for purposes of the present invention include, but are not limited to, any type of scope, flexible or rigid (e.g., endoscope, arthroscope, bronchoscope, choledochoscope, colonoscope, cystoscope, duodenoscope, gastroscope, hysteroscope, laparoscope, laryngoscope, neuroscope, otoscope, push enteroscope, rhinolaryngoscope, sigmoidoscope, sinuscope, thorascope, etc.) and any device similar to a scope that is equipped with an image system (e.g., a nested cannula with imaging). The imaging is local, and surface images may be obtained optically with fiber optics, lenses, and miniaturized (e.g. CCD based) imaging systems.

In practice, endoscope 12 is mounted to the end-effector of robot 11. A pose of the end-effector of robot 11 is a location and an orientation of the end-effector within a coordinate system of an actuator of robot. With endoscope 12 mounted to the end-effector of robot 11, any given pose of a field-of-view ("FOV") of endoscope 12 within an anatomical region corresponds to a distinct pose of the end-effector of robot 11 within the robotic coordinate system. Consequently, each distinct individual endoscopic image of the anatomical region generated by endoscope 12 may be linked to a corresponding pose of endoscope 12 within the robotic coordinate system.

Video capture device 13 is broadly defined herein as any device structurally configured with a capability to convert an endoscopic video signal from endoscope 12 into a computer readable temporal sequence of endoscopic image frames ("EIF") 14. In practice, video capture device 13 may employ a frame grabber of any type for capturing individual digital still frames from the endoscopic video signal.

Figure 1:
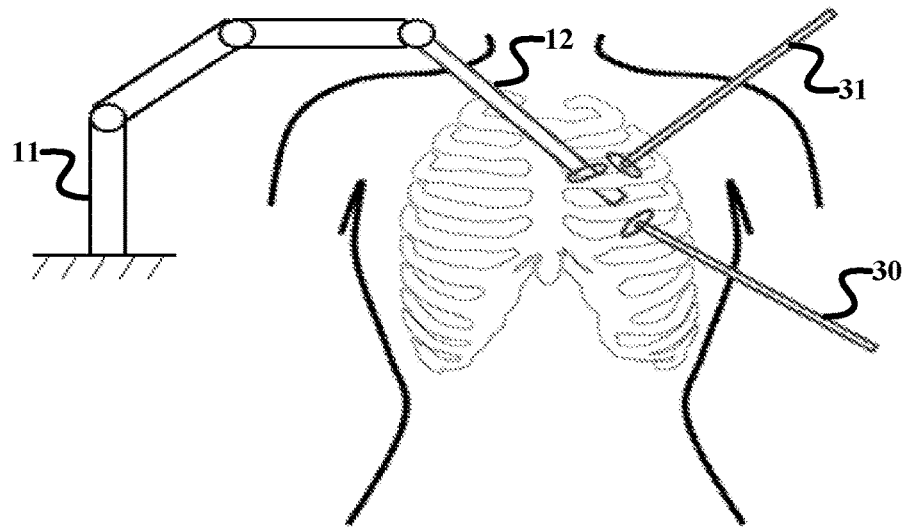
FIG. 1 illustrates an exemplary robotic control of an endoscope during a surgical procedure as known in the art

Still referring to FIG. 1, control unit 20 includes a robot controller 21 and an endoscopic image controller 25.

Robot controller 21 is broadly defined herein as any controller structurally configured to provide one or more robot actuator commands ("RAC") 29 to robot 11 as known in the art for controlling a pose of the end-effector of robot 11 as desired for the endoscopic procedure. More particularly, robot controller 21 employs an operator command module ("OCM") 22 for converting operator pose commands ("OPC") 25 from an operator of control unit 20 into robot actuator commands 29 as known in the art, and further employs an image command module ("ICM") 23 for converting endoscope pose commands ("EPC") 28 from endoscopic image controller 25 into robot actuator commands 29 as will be further explained in connection with description of FIGS. 3-7.

For example, operator pose command(s) 27 may indicate an endoscopic path leading to a desired 3D pose of the FOV of endoscope 12 within the anatomical region whereby robot controller 21 converts operator pose command(s) 27 into robot actuator commands 29 including an actuation current for each motor of robot 11 as needed to move (i.e. translate and/or rotate) endoscope 12 to the desired 3D pose of the FOV of endoscope 12 within the anatomical region. By further example, endoscope pose command(s) 28 may indicate an instrument visibility control upon the FOV of endoscope 12 reaching the desired 3D pose whereby robot controller 21 converts endoscope pose command(s) 28 into robot actuator commands 29 including an actuation current for each motor of robot 11 as needed to move (i.e. translate, and/or rotate) endoscope 12 to maintain instrument visibility in the FOV of endoscope 12.

Endoscopic image controller 25 is broadly defined herein as any controller structurally configured for controlling an endoscopic image display of endoscopic image frames 14 as known in the art. For purposes of the present invention, the endoscopic image display is broadly define to include an operator viewing of a display of endoscopic image frames 14 via an eyepiece (not shown) of endoscope 12 and/or by a screen monitor (not shown) for videoscope embodiments of endoscope 12.

Figure 3:
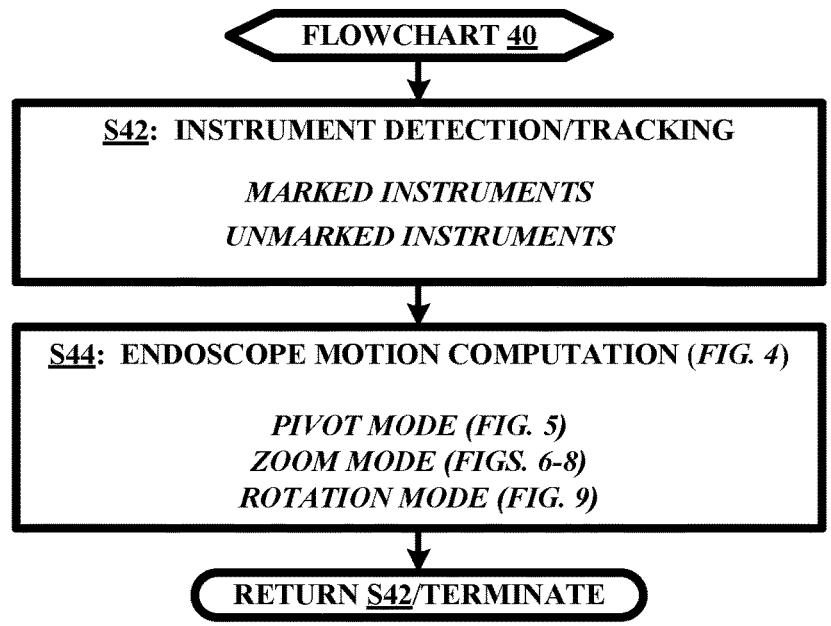
FIG. 3 illustrates a flowchart representative of an exemplary embodiment of an instrument visibility control method in accordance with the present invention.
Figure 4:
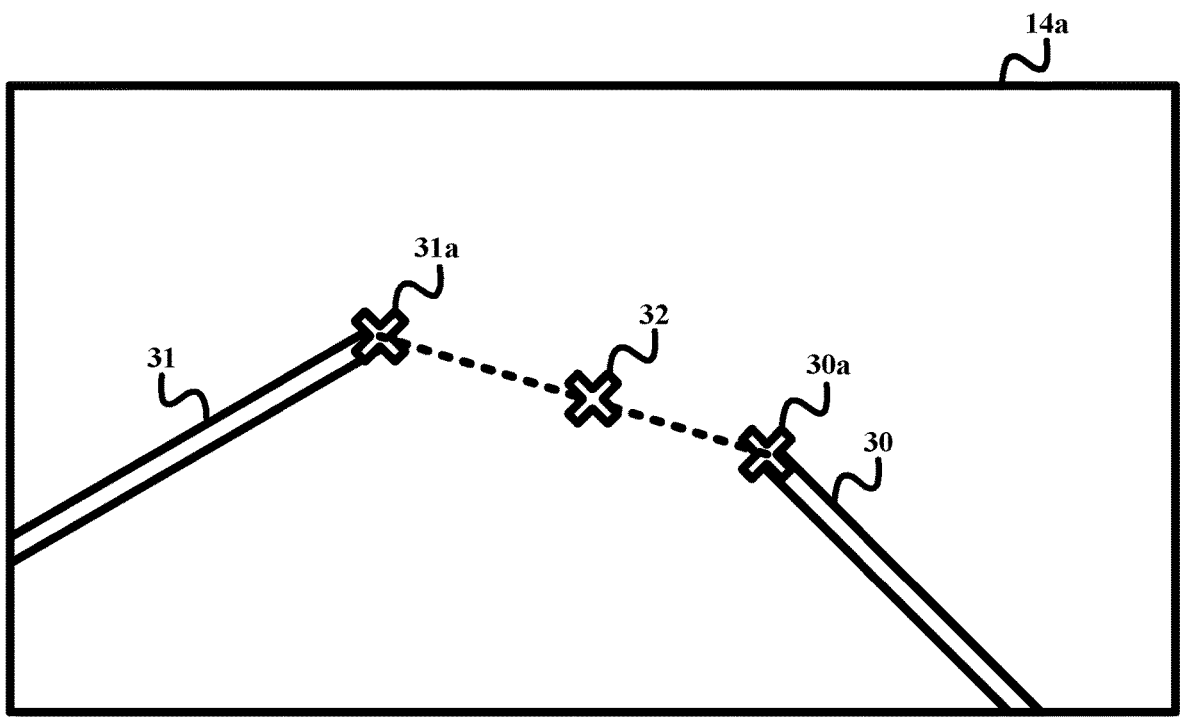
FIG. 4 illustrates an exemplary endoscopic field of view in accordance with the present invention.

To address the visibility control of instruments as previously described herein in connection with FIG. 1, endoscopic image controller 25 employs a visibility control module ("VCM") 26 structurally configured for generating endoscope pose command(s) 28 to maintain visibility of instruments with a FOV of endoscope 12, calibrated or uncalibrated, in accordance with a flowchart 40 of FIG. 3.

Referring to FIG. 3, a stage S42 of flowchart 40 encompasses visibility control module 26 (FIG. 2) detecting and tracking instrument(s) within the FOV of endoscope 12 (FIG. 2) as known in the art, and a stage S44 of flowchart 40 encompasses module 23 computing endoscope motion parameters to maintain the visibility of the detected/tracked instrument(s) within the FOV of endoscope 12 based on a selection of spatial point between the instruments. For example, as shown in an endoscopic image 14a of FIG. 4, a spatial point (e.g., midpoint) between distal tips 30a and 31a of respective instruments 30 and 31 is selected whereby robot 11 (FIG. 2) is controlled to move endoscope 12 (FIG. 2) (e.g., lateral, longitudinal and/or rotational) to thereby position the spatial point at a center 33 of endoscopic image 14a. In practice, flowchart 40, may be performed automatically with every motion of the instruments, or may be invoked by an operator of control unit 20 via an input device (e.g., a button on the instrument, a foot pedal, voice command, etc.).

In embodiments of stage S42, marked or unmarked instruments may be detected and tracked as known in the art.

Figure 5A:
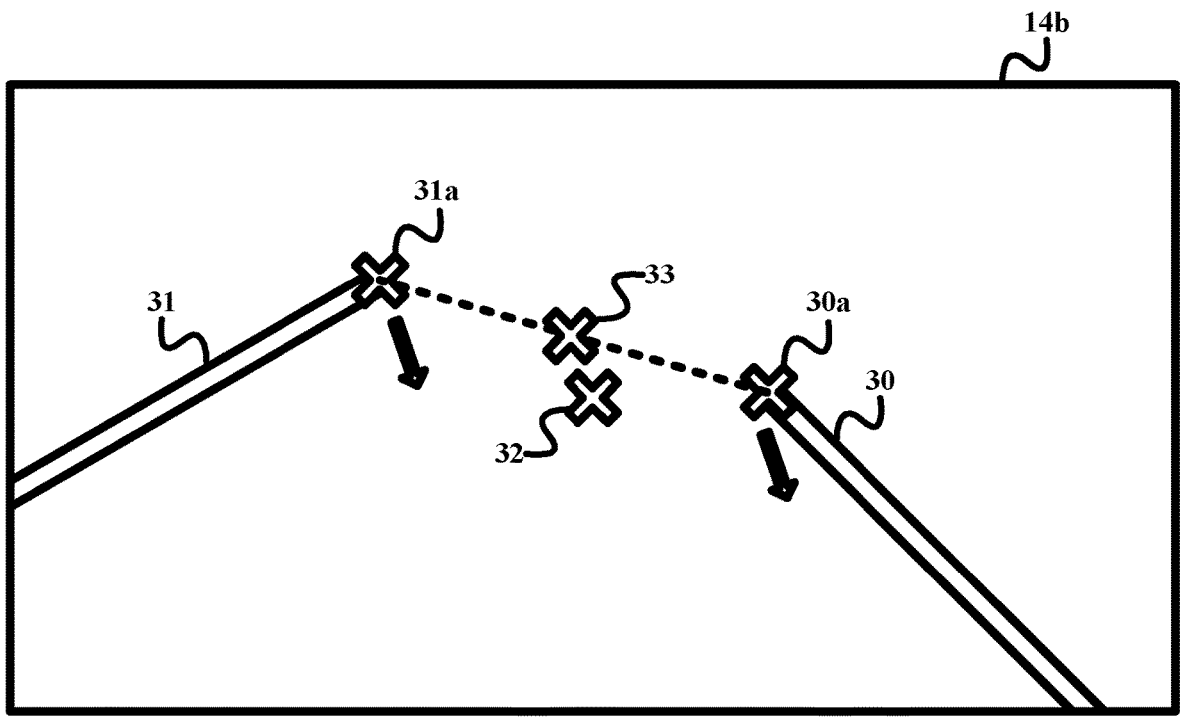
FIG. 5 illustrates an exemplary pivot mode of instrument visibility control method shown in FIG. 3.
Figure 5B:
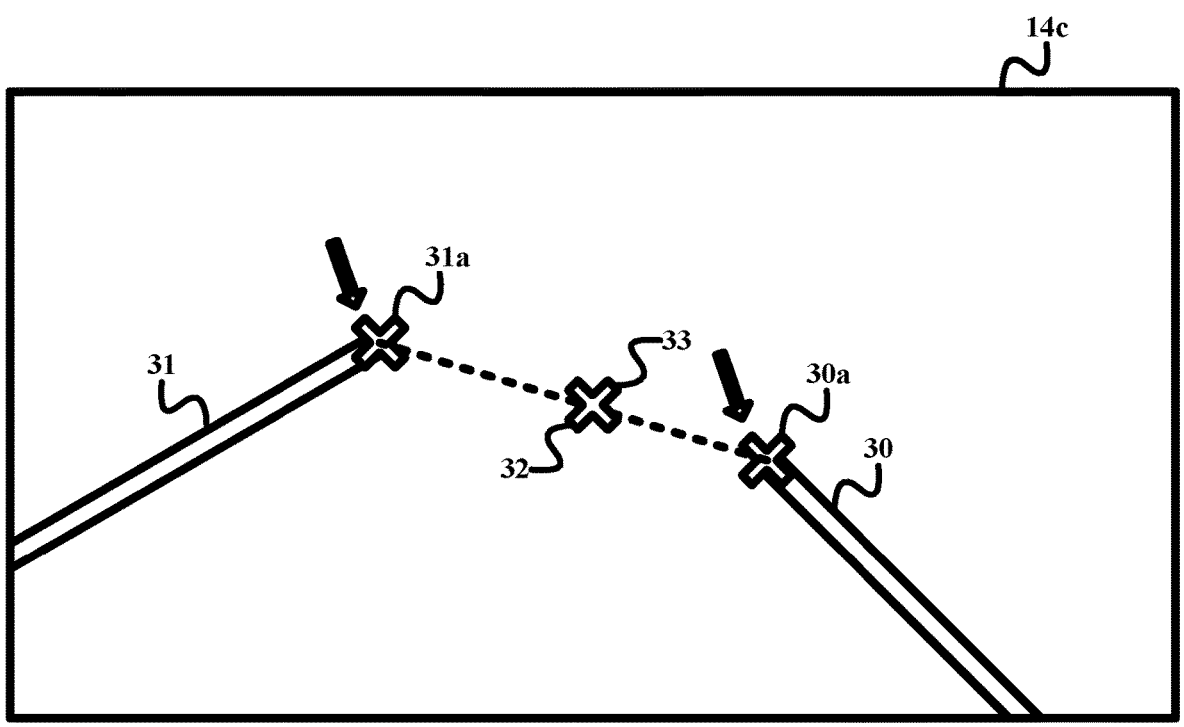

In pivot mode embodiments of stage S44, the zoom and rotational angle are assumed to be appropriate whereby the robot 11 is controlled to laterally move endoscope 12 to thereby align a spatial point between the instruments to the center of endoscopic image. For example, as shown in FIG. 5A, an endoscopic view 14b shows a spatial midpoint 33 of distal tips 30a and 31a being spaced from a center of endoscopic view 14b. Accordingly, robot 11 is controlled to pivot endoscope 12 as indicated by the arrows to thereby align spatial midpoint 33 with center 33 of endoscopic view 14c.

In practice, if the control operator wishes to keep both instruments within the FOV of endoscope 12 but considers an importance of one instrument higher than the other instrument, then the spatial point upon which robot 11 keeps within the center of the endoscopic image may be at any location on a virtual line between the two instruments. For example, spatial point 33 of FIG. 5 may be closer to distal tip 30a than distal tip 31a if the visibility of instrument 30 is considered to be important or higher priority than the visibility of instrument 31.

Figure 6A:
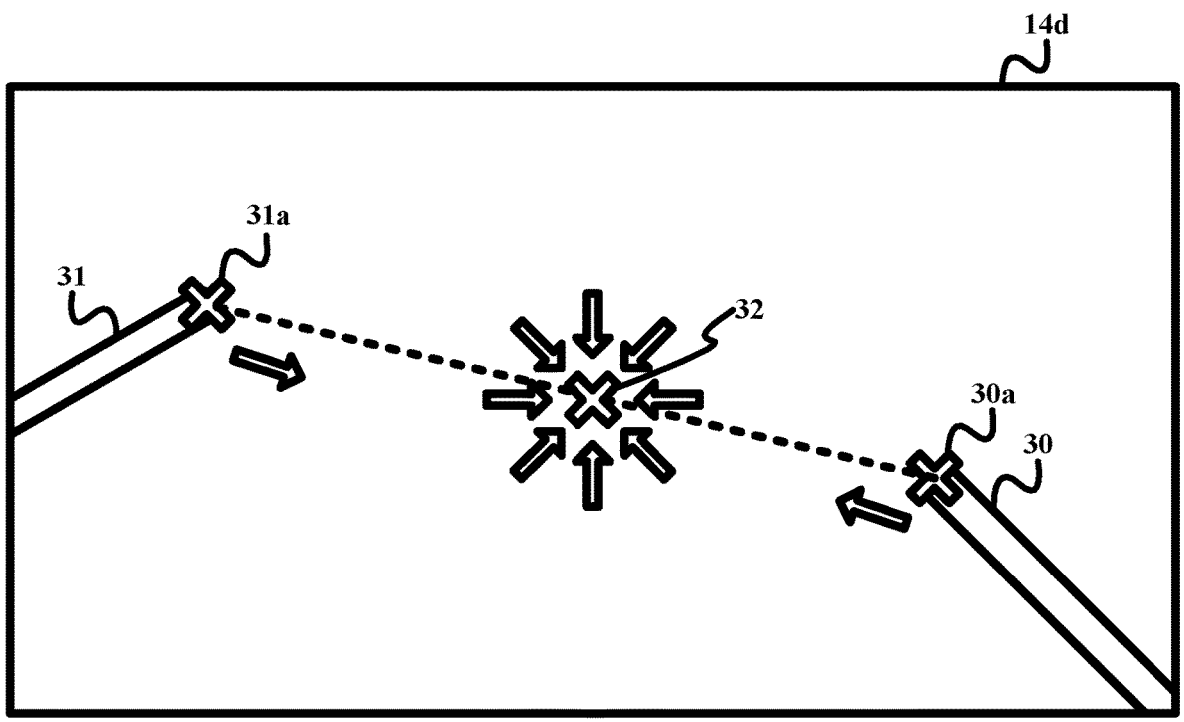
FIG. 6 illustrates an exemplary zoom mode of instrument visibility control method shown in FIG. 3.
Figure 6B:
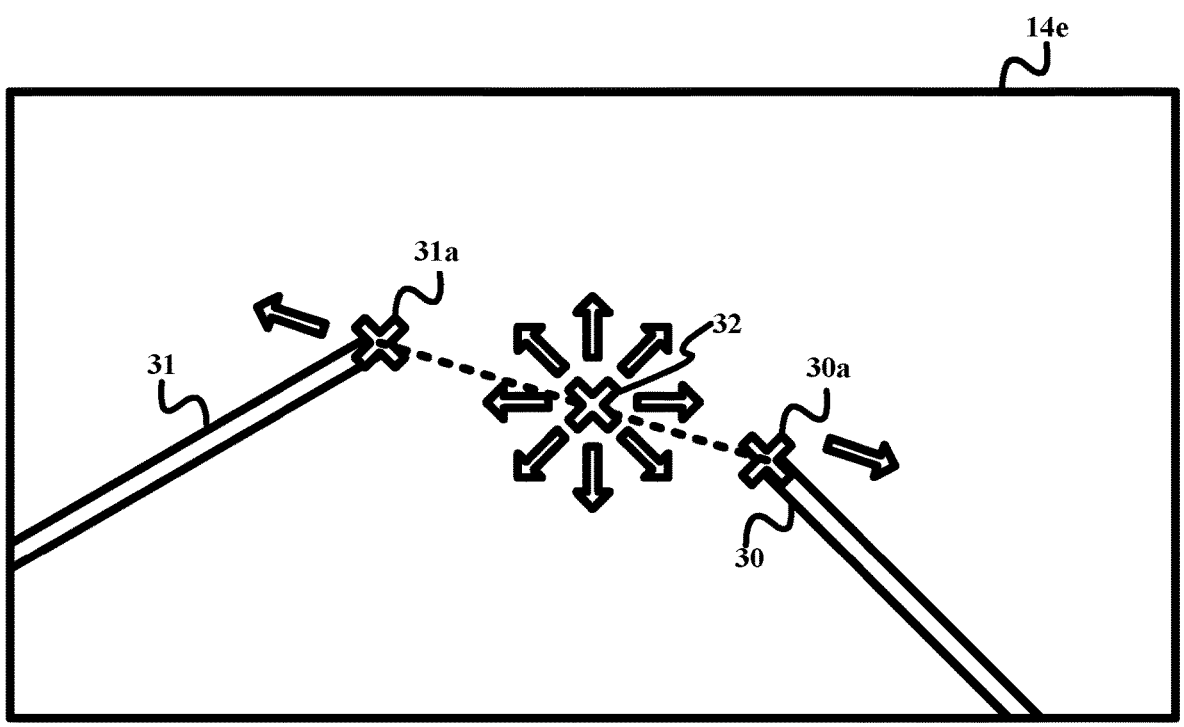
Figure 7:
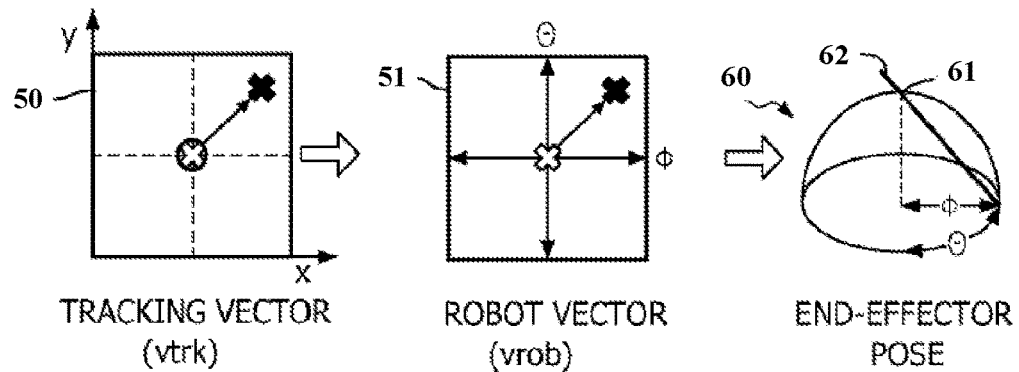
FIG. 7 illustrates an exemplary tracking of an uncalibrated endoscope as known in the art.

In zoom mode embodiments of stage S44 (FIG. 2), the lateral positioning and rotational angle are assumed to be appropriate whereby the robot 11 is controlled to longitudinally move endoscope 12 to thereby maintain an alignment of a spatial point between the instruments at the center of endoscopic image when the instruments are being moved toward or away from each other. For example, FIG. 6A illustrates arrows for zooming in instruments 30 and 31 by longitudinally moving endoscope 12 towards center 32 of endoscopic image 14d as instruments 30 and 31 are being moved toward each other, and FIG. 6B illustrates arrows for zooming out instruments 30 and 31 by longitudinally moving endoscope 12 away from center 32 of endoscopic image 14e as instruments 30 and 31 are being moved away from each other.

Specifically, one zooming technique for endoscope 12 implements a 'pinch-to-zoom' gesture used to zoom in and out on touch-screen enabled personal devices. Specifically, when this control mode is activated, a virtual line is drawn between the two instrument tips 30a and 31a as exemplary shown in FIG. 6. Moving the two instrument tips either towards the center of the image by pinching opposing arrows toward each other as shown in FIG. 6A or moving the two instrument tips away from the center of the image by pinching opposing arrows away from other as shown in FIG. 6B (thus varying the distance between the tips) is used to control the motion of the endoscope along its principal axis. A decrease in the distance between tips could cause a translation of the endoscope along the principal axis, thus bringing the endoscope closer to the instruments, or vice versa.

Figure 8:
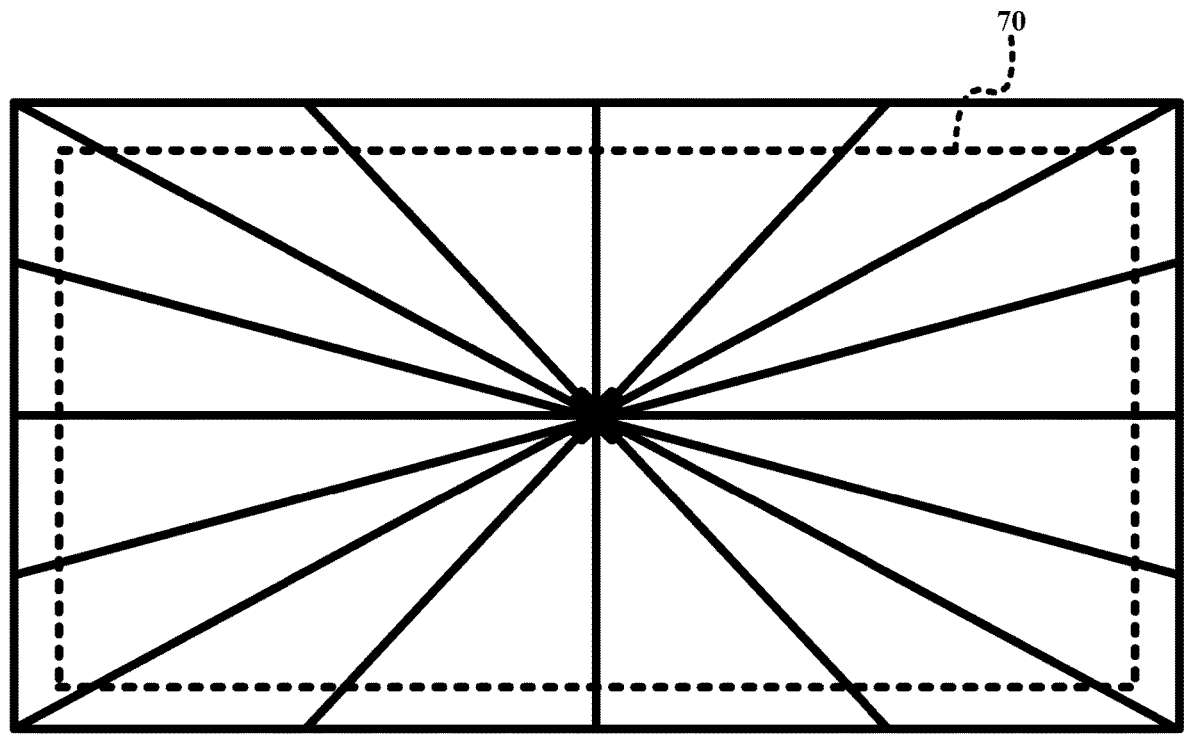
FIG. 8 illustrates an exemplary zoom border in accordance with the present invention.
Figure 9A:
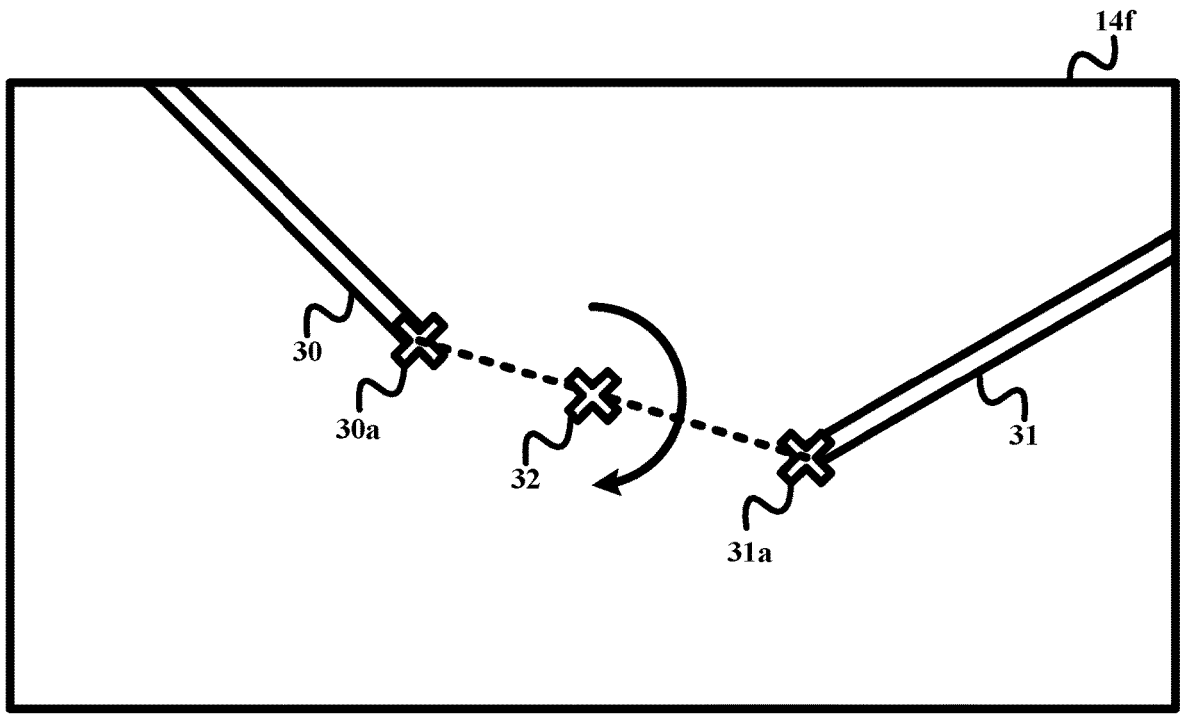
FIG. 9 illustrates an exemplary rotation mode of instrument visibility control method shown in FIG. 3.
Figure 9B:
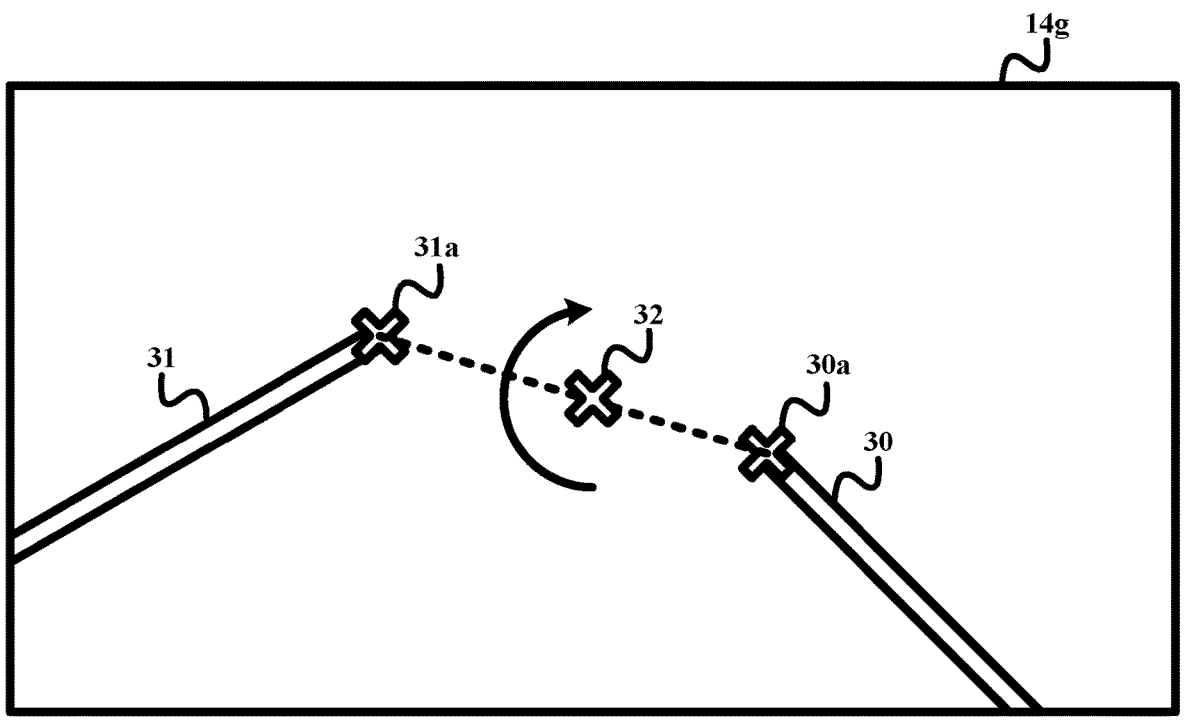

More particularly, a tracking vector 50 of a tracked point of an instrument (e.g., a distal tip of the instrument) is used to construct a robot vector 51 and transform it to end effector pose 60 described as two angles ($\varphi$, $\theta$) around an insertion point 61 for endoscope 62. A motion of endoscope 62 along its principal axis (i.e. in and out from insertion point 61) will also generate a tracking vector describing motion of the instrument tracked point in the image as a result of motion of the endoscope 61. In a simplest case, if assuming an image plane is perpendicular to endoscope axis, the instrument will be moving on the image along rays radiating from the image center and tracking vector (vtrk) 50 will be along these rays. Consequently, the known velocity optimization scheme may be used this motion with the understanding that (1) a direction of the robot motion is always known and it is always out (zoom-out) and a robot stop criterion is when the instrument moves across the limit of border area (e.g., a border area 70 as shown in FIG. 8).

In rotational mode embodiments of stage S44 (FIG. 2), the lateral positioning and zoom angle are assumed to be appropriate whereby the robot 11 is controlled to rotate endoscope 12 along an alignment of a spatial point between the instruments to the center of endoscopic image as instruments 30 and 31 are rotated relative to each other within the anatomical region.

Referring back to FIG. 1, in practice, endoscope pose commands 28 may have the same or analogous form as operator pose commands 27. Specifically, module 26 similar to an input module of a joystick determines and communicates the appropriate lateral/longitudinal movement and/or rotational degrees for endoscope 12 to module 24. Alternatively, endoscope pose commands 28 may indicate a degree of misalignment and/or rotational offset of instruments to the center of the endoscopic image and module 24 performs any necessary calculations of the appropriate lateral/longitudinal movement and/or rotational degrees for endoscope 12.

From the description of FIGS. 2-7 herein, those having ordinary skill in the art will appreciate the numerous benefits of the present invention including, but not limited to, guidance of a robotic endoscope whereby instrument(s) are always visible at the appropriate rotational angle within a field of view of the robotic endoscope.

While various embodiments of the present invention have been illustrated and described, it will be understood by those skilled in the art that the embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:
1. A robot guiding system, comprising:
   a robot unit including
      an endoscope operable to generate an endoscopic image of an anatomical region, and
      a robot operably connected to the endoscope to move the endoscope within the anatomical region responsive to robotic actuator commands; and
   a control unit including
      an endoscopic image controller operably connected to the endoscope to control a display of the endoscopic image of the anatomical region,
         wherein the endoscopic image controller is configured to generate endoscope pose commands to maintain a visibility of at least two interventional instruments within the display of the endoscopic image relative to a center of the endoscopic image by aligning a selected spatial point, positioned on a virtual line connecting distal tips of the at least two interventional instruments, with the center of the endoscopic image, and
      a robot controller operably connected to the robot and the endoscopic image controller to generate the robotic actuator commands responsive to the endoscope pose commands to cause the robot to move the endoscope to align the spatial point with the center of the endoscopic image.
2. The robot guiding system of claim 1, wherein spatial point is at a midpoint of the virtual line connecting the distal tips of the two interventional instruments.

3. The robot guiding system of claim 1, wherein the spatial point is offset from a midpoint of the virtual line connecting the distal tips of the two interventional instruments.

4. The robot guiding system of claim 1, wherein the endoscopic image controller generates the endoscope pose commands to pivot the endoscope as required to maintain an alignment of the spatial point between the at least two interventional instruments to the center of the endoscopic image.

5. The robot guiding system of claim 1, wherein the endoscopic image controller is configured to generate the endoscope pose commands to longitudinally move the endoscope as required to maintain the visibility of the two interventional instruments within the display of the endoscopic image relative to the center of the endoscopic image responsive to the two interventional instruments being moved toward each other within the anatomical region.

6. The robot guiding system of claim 1, wherein the endoscopic image controller is configured to generate the endoscope pose commands to longitudinally move the endoscope as required to maintain the visibility of the two interventional instruments within the display of the endoscopic image relative to the center of the endoscopic image responsive to the at least two interventional instruments being moved away from other within the anatomical region.

7. The robot guiding system of claim 1, wherein the endoscopic image controller generates the endoscope pose commands to rotate the endoscope as required to maintain the visibility of at least two interventional instruments within the display of the endoscopic image relative to a center of the endoscopic image responsive to the at least two interventional instruments being rotated relative to each other within the anatomical region.

8. The robot guiding system of claim 1, wherein the endoscope is uncalibrated.

9. A control unit for a robot connected to an endoscope generating an endoscopic image of an anatomical region, the control unit comprising:
an endoscopic image controller operable to control a display of the endoscopic image of the anatomical region,
wherein the endoscopic image controller is configured to generate endoscope pose commands to maintain a visibility of at least two interventional instruments within the display of the endoscopic image relative to a center of the endoscopic image by aligning a selected spatial point positioned on a virtual line connecting distal tips of the at least two interventional instruments with the center of the endoscopic image; and
a robot controller operably connected to the endoscopic image controller to generate robotic actuator commands responsive to the endoscope pose commands to control a robot to move the endoscope to align the spatial point with the center of the endoscopic image.

10. The control unit of claim 9, wherein the endoscopic image controller generates the endoscope pose commands to pivot the endoscope as required to maintain an alignment of the spatial point between the at least two interventional instruments to the center of the endoscopic image.

11. The control unit of claim 9,
wherein the endoscopic image controller is configured to generate the endoscope pose commands to longitudinally move the endoscope as required to maintain visibility of the at least two interventional instruments within the display of the endoscopic image relative to the center of the endoscopic image responsive to the at least two interventional instruments being moved toward each other within the anatomical region; and
wherein the endoscopic image controller is configured to generate the endoscope pose commands to longitudinally move the endoscope as required to maintain visibility of the at least two interventional instruments within the display of the endoscopic image relative to the center of the endoscopic image responsive to the at least two interventional instruments being moved away from each other within the anatomical region.

12. The control unit of claim 9, wherein the endoscopic image controller generates the endoscope pose commands to rotate the endoscope as required to maintain the visibility of at least two interventional instruments within the display of the endoscopic image relative to a center of the endoscopic image responsive to the at least two interventional instruments being rotated relative to each other within the anatomical region.

13. A robot guiding method, comprising:
operating an endoscope to generate and display an endoscopic image of an anatomical region; and
commanding a robot to move the endoscope within the anatomical region as the endoscope is generating the endoscopic image of the anatomical region,
wherein the commanding of the robot maintains a visibility of at least two interventional instruments within the display of the endoscopic image relative to a center of the endoscopic image by aligning a selected spatial point positioned on a virtual line connecting distal tips of the at least two interventional instruments with the center of the endoscopic image.

14. The robot guiding method of claim 13, wherein the robot is commanded to pivot the endoscope as required to maintain an alignment of the spatial point between the at least two interventional instruments to the center of the endoscopic image.

15. The robot guiding method of claim 13,
wherein the robot is commanded to longitudinally move the endoscope as required to maintain visibility of the at least two interventional instruments within the display of the endoscopic image relative to the center of the endoscopic image responsive to the at least two interventional instruments being moved toward each other within the anatomical region; and
wherein the robot is commanded to longitudinally move the endoscope as required to maintain visibility of the at least two interventional instruments within the display of the endoscopic image relative to the center of the endoscopic image responsive to the at least two interventional instruments being moved away from other within the anatomical region.

16. The robot guiding method of claim 13, wherein the robot is commanded to rotate the endoscope as required to maintain the visibility of at least two interventional instruments within the display of the endoscopic image relative to a center of the endoscopic image responsive to the at least two interventional instruments being rotated relative to each other within the anatomical region.

* * * * *